United States Patent [19]

Mazur et al.

[11] Patent Number: 5,120,412
[45] Date of Patent: Jun. 9, 1992

[54] PREPARATION OF HYPERICIN

[75] Inventors: Yehuda Mazur, Rehovot, Israel; Harald Bock, Berlin, Fed. Rep. of Germany; David Lavie, Rehovot, Israel

[73] Assignee: Yeda Research and Development Co. Ltd., Rehovot, Israel

[21] Appl. No.: 613,604

[22] Filed: Nov. 9, 1990

[30] Foreign Application Priority Data

Nov. 15, 1989 [IL] Israel ........................................ 92315

[51] Int. Cl.$^5$ .................... C07C 51/00; C07C 401/00; C07C 50/36; A61K 31/12
[52] U.S. Cl. .......................... 204/157.87; 204/157.88; 204/157.91; 552/282
[58] Field of Search ................... 552/282; 204/157.87, 204/157.88, 157.91

[56] References Cited

U.S. PATENT DOCUMENTS 1,935,721  11/1933  Kunz et al. ........................... 552/282
2,707,704   5/1955  Brockmann et al. ........... 204/157.91

FOREIGN PATENT DOCUMENTS 0432496  6/1991  European Pat. Off. .

OTHER PUBLICATIONS

"Synthese des Proto-hypericins und Hypericins aus Emodin-antron-(9)," Brockmann, H., et al., *Chemische Berichte*, vol. 91, No. 3, Mar. 1958, pp. 547-553.
"Reactions concerned in tertiary amine N-oxides, XV. Dimerization reactions of anthrone and its derivatives using pyridine N-oxide as oxidizing reagent," Haginiwa, J. et al., *Chemical Abstracts*, No. 87785a, Columbus, OH, U.S., vol. 99, No. 11, Sep. 12, 1983, p. 532.

*Primary Examiner*—John Niebling
*Assistant Examiner*—Steven P. Marquis
*Attorney, Agent, or Firm*—Browdy and Neimark

[57] ABSTRACT

A process for preparing hypericin comprises oxidative dimerization of emodin anthrone and conversion of the intermediate protohypericin to hypericin by irradiation with visible light.

9 Claims, No Drawings

PREPARATION OF HYPERICIN

This invention provides a novel process for the synthesis of the natural substance hypericin having the following formula

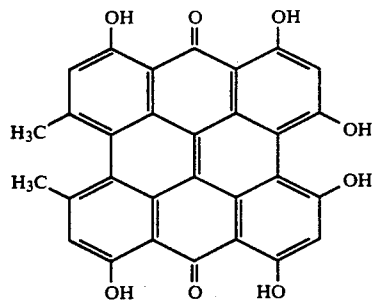

BACKGROUND OF THE INVENTION

Hypericin is a constituent of plants belonging to the genus Hypericum. It was isolated from this natural source in a chemically pure state by H. Brockmann et al. (Ann. 1942, 553, 1). Hypericin always appears in nature accompanied by the chemically related compound pseudo-hypericin.

Hypericin has gained interest in the last few years by virtue of the discovery of its anti-viral and anti-retroviral activity (cf., inter alia, European Patent Application No. 0 256 452 and G. Lavie et al., Proc. Natl. Acad. Sci. U.S.A. 1989, 86, 596). Hypericin is now considered as a potentially effective drug against a number of diseases caused by the above-mentioned viruses.

The isolation of hypericin from Hypericum plants is not feasible on a larger scale, because it requires a lengthy procedure involving extraction with large volumes of solvents and cumbersome chromatographic separations on silica gel columns. The main difficulty in obtaining hypericin in a pure state from the plant material resides in its separation from the accompanying pseudohypericin. This necessitates the aforementioned chromatography with the elution of a large number of fractions, only a few of which contain the pure desired material. The yield of hypericin from the plants is very low, not more than 0.3%, based on the dry plant material.

A number of synthetic routes for hypericin have also been reported. One is a total synthesis starting from 3,5-dimethoxybenzoic acid methyl ester and requiring 12 process steps with an overall yield of ca. 6-9% (H. Brockman et al., Chem. Ber. 1957, 90, 2302).

The other syntheses use commercially available emodin as a starting material (for structure cf. Reaction Scheme). Emodin can be converted directly to protohypericin, a substituted helianthrone derivative which, on irradiation with visible light, is converted to hypericin. The first conversion involves treating a solution of emodin in aqueous base in the presence of hydroquinone in a sealed ampoule for 3 weeks at 120° C. (H. J. Banks et al., Aust. J. Chem. 1976, 29, 1509; D. Spitzner, Angew. Chem. Int. Ed. Engl. 1977, 16, 46; G. Rodewald et al., ibid. 1977, 16, 46). The reported yield of protohypericin is not more than 29%. Besides this low yield, this synthesis has other drawbacks, namely the experimental difficulty in up-scaling this reaction, the large volumes of solvents needed for extraction, and the lengthy chromatographic separation.

Other syntheses also utilize emodin which is reduced to emodin anthrone (cf. Reaction Scheme). The latter can be oxidized to protohypericin in pyridine solution in the presence of piperidine. However, the yield of protohypericin and thus also of the derived hypericin was reported to be lower than ca. 10% (H. Brockman et al., Chem. Ber. 1958, 91, 547). This low yield necessitates special separation procedures which renders this method unsuitable for large scale production of hypericin.

REACTION SCHEME

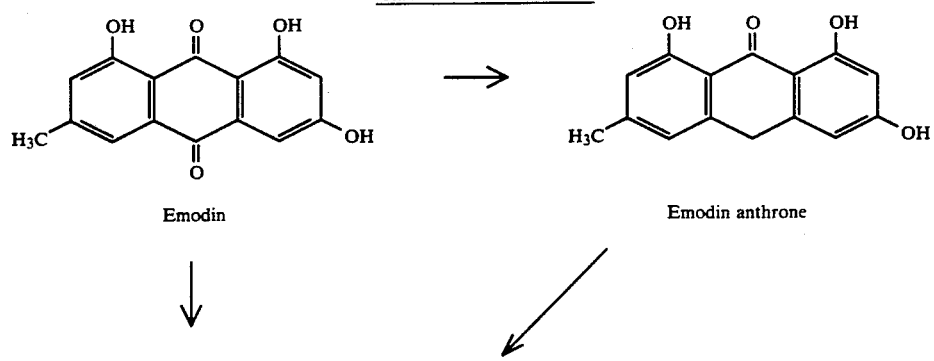

-continued
REACTION SCHEME

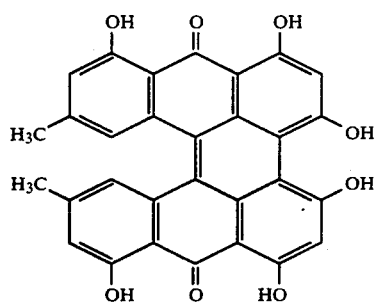

Protohypericin

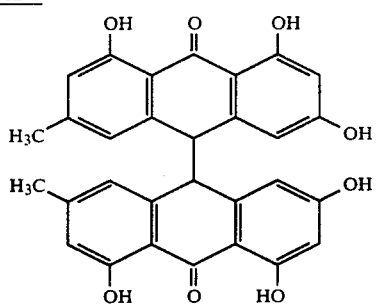

Emodin bianthrone

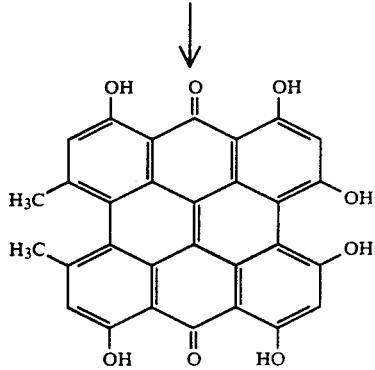

Hypericin

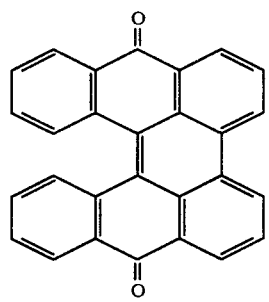

Helianthrone

Alternatively, emodin anthrone can be oxidized to emodin bianthrone (cf. Reaction Scheme) which, in basic solution in the presence of air, yields protohypericin. The latter reaction could be successfully performed only on a very small scale (on ca. 10 mg). (D. W. Cameron et al,. Aust. J. Chem. 1976, 29, 1535; H. J. Banks et al., Aust. J. Chem. 1976, 29, 1509).

There exists, thus, an increasing need for a simple, efficient and economically feasible process for the synthesis of hypericin in comparatively high amounts, which process should avoid all the above-mentioned drawbacks of the prior art processes. It is the object of the present invention to fulfill this need.

SUMMARY OF THE INVENTION

The above object is achieved by the present invention, which provides a process for preparing hypericin of the formula

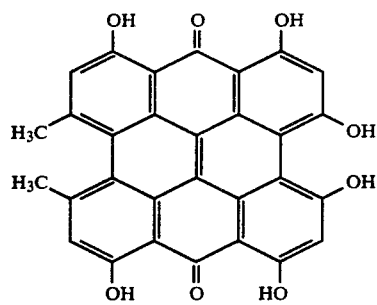

which comprises oxidative dimerization of emodin anthrone of the formula

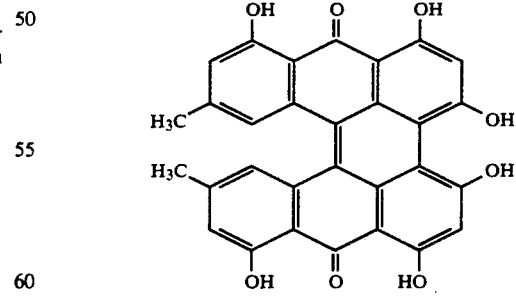

by reacting it with an oxygen transfer reagent in a solvent selected from tertiary aromatic amines, in the presence of a conventional redox catalyst and a secondary amine to yield protohypericin of the formula

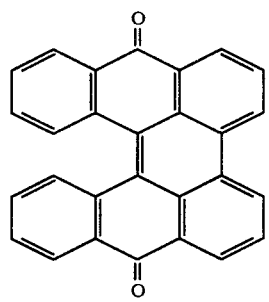

and converting the protohypericin thus obtained to hypericin by irradiation with visible light.

This novel process according to the invention overcomes all the drawbacks of the previously disclosed hypericin syntheses and is, therefore, suitable for the production of this compound in the large amounts required for its potential use as an anti-viral drug.

DETAILED DESCRIPTION OF THE INVENTION

The process of the present invention uses as a starting material emodin anthrone which is obtainable in high yields by known method from the commercially available emodin (cf. R. A. Jacobson et al., J. Amer. Chem. Soc. 1924, 46, 1312 and R. Kinget, Planta Med. 1967, 15, 233). The structure of both compounds is shown in the above Reaction Scheme.

It has been found in accordance with the present invention that emodin anthrone can be converted in high yield to protohypericin under selected specific conditions, namely, treating a solution of emodin anthrone in a tertiary amine, preferably pyridine, containing a secondary amine, preferably piperidine, with a tertiary amine oxide, preferably pyridine N-oxide in the presence of a conventional redox catalyst, preferably ferrous sulfate. As stated above, irradiation with visible light converts the resulting protohypericin quantitatively to the desired hypericin.

It was reported previously by J. Haginiwa et al., Yakugaku Zasshi 1983, 103, 273-278, that 2-methoxy-1-hydroxyanthrone can be dimerized by pyridine N-oxide in the presence of ferrous sulfate, to yield a dimethoxy dihydroxy derivative of helianthrone (for structure cf. Reaction Scheme above). However, the inventors of the present invention found that when these reaction conditions were applied to emodin anthrone, no protohypericin was formed, indicating that the above reaction is unsuitable for hypericin synthesis.

It was, therefore, surprising to find, in accordance with the present invention, that when emodin anthrone in pyridine solution is heated under exclusion of air with pyridine N-oxide in the presence of piperidine and a catalytic amount of ferrous sulfate, protohypericin was formed in ca. 70% yield. This compound could be isolated directly from the reaction mixture without the need for extraction procedures or chromatographic separations. When any one of the aforementioned reagents or solvents (pyridine, piperidine, pyridine N-oxide or ferrous sulfate) are absent from the reaction mixture, the yield of protohypericin is very small or even nil. The presence of air in the reaction mixture also considerably diminishes the yield of the aforesaid product.

The inventors have also found that pyridine N-oxide and ferrous sulfate in a neutral, polar or non-polar solvent or in acidic solvents (such as acetic acid) do not convert emodin anthrone to protohypericin.

As stated above, pyridine N-oxide is a preferred oxygen transfer reagent in the process according to the invention. However, other tertiary amine N-oxides (such as pyridazine N-oxide, pyrazine N-oxide, dimethylaniline N-oxide) or other oxygen transfer reagents, such as iodosobenzene, can be successfully used to convert emodin anthrone to protohypericin in high yield.

Among the conventional redox catalysts which are suitable for use in the process according to the invention, there may be mentioned divalent and trivalent nickel, iron and cobalt salts, especially sulfates or halides, e.g. chlorides. Among such salts, ferrous sulfate is a preferred catalyst. Alternatively, Group VIII metals, such as palladium or platinum on charcoal, can also be used as catalysts in this reaction.

Various tertiary aromatic amines can be used as solvents in the process of the present invention, pyridine being preferred. Similarly, the secondary amine which must be present in the reaction mixture of the process according to the invention, can be selected from a wide variety of such compounds, piperidine being preferred.

In accordance with a preferred embodiment of the invention, the process is conducted by heating emodin anthrone for about 1 hour under reflux (about 100° C.) in a 5% solution in a solvent mixture consisting of pyridine and piperidine in a proportion of 10:1 by volume, the solution containing 5-6 mole equivalents of pyridine N-oxide and catalytic amounts of ferrous sulfate heptahydrate (about 0.1 mole equivalent). The resulting dark violet solution is evaporated to dryness at a reduced pressure, the residue is dissolved in acetone and irradiated with visible light overnight to yield hypericin.

The invention is illustrated in the following Example 1, it being understood that the scope of the invention should not be limited thereto. Example 2 is a control example and the process described therein does not form part of the present invention.

EXAMPLE 1

Emodin anthrone, 2 g, was dissolved in a mixture of 40 mL pyridine and 4 mL piperidine. To the resulting solution there were added 4 g of pyridine N-oxide and 0.1 g of ferrous sulfate heptahydrate and the reaction mixture was refluxed for 1 hr. at (100° C.). The mixture was then concentrated under vacuum (25 mm Hg) to a volume of 5 ml, the residue was mixed with 100 ml of 3% aqueous hydrochloric acid upon which a dark precipitate formed. This precipitate was filtered off and washed with water until the washings were neutral. The obtained material was dissolved in 400 mL of acetone and the filtered solution irradiated with a halogen lamp (500 watt) overnight. The acetone solution was then concentrated to a volume of 50 mL and then triturated with 500 mL of hexane. The formed precipitate was filtered off. It consisted of 1.25 g of hypericin (63%) yield, $\lambda_{max}$588 nm ($\epsilon$46000), 545 nm ($\epsilon$23000), 325 nm ($\epsilon$30,000).

EXAMPLE 2

To emodin anthrone, 2 g, there were added 4 g of pyridine N-oxide and 0.1 g of ferrous sulfate heptahydrate and the reaction mixture was heated for 1 hr. The resulting material was treated as described in Example 1 above to yield a green solid. Chromatographic analysis of this solid did not reveal the presence of protohypericin or hypericin.

We claim:

1. A process for preparing hypericin of the formula

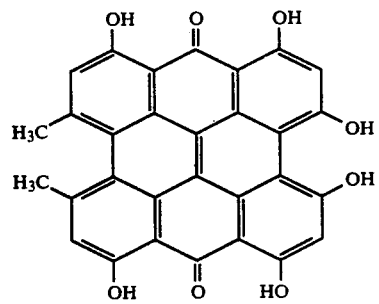

which comprises oxidative dimerization of emodin anthrone of the formula by reacting it with an oxygen transfer reagent in a sol-

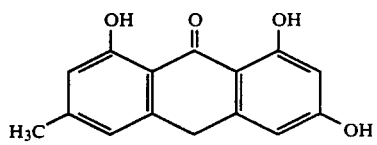

vent selected from tertiary aromatic amines, in the presence of a conventional redox catalyst and a secondary amine to yield protohypericin of the formula

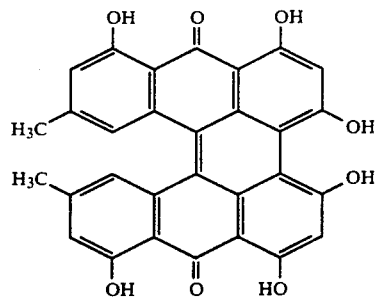

and converting the protohypericin thus obtained to hypericin by irradiation with visible light.

2. A process according to claim 1, wherein said oxygen transfer reagent is a tertiary amine oxide selected from pyridine N-oxide, pyridazine N-oxide, pyrazine N-oxide and N,N-dimethylaniline N-oxide.

3. A process according to claim 2, wherein said tertiary amine oxide is pyridine N-oxide.

4. A process according to claim 1, wherein said solvent is pyridine.

5. A process according to claim 1, wherein said secondary amine is present in a proportion of about 1 part by weight to about 10 parts by weight of the solvent.

6. A process according to claim 1, wherein said secondary amine is piperidine.

7. A process according to claim 1, wherein said redox catalyst is selected from sulfate and halide salts of $Ni^{+2}$, $Ni^{+3}$, $Fe^{+2}$, $Fe^{+3}$, $Co^{+2}$ and $Co^{+3}$ and palladium and platinum metals on charcoal.

8. A process according to claim 7, wherein said redox catalyst is ferrous sulfate.

9. A process according to claim 1, wherein about 5-6 mole equivaltents of said tertiary amine oxide are used per mole equivalent of emodin anthrone.

* * * * *